(12) United States Patent
Guibert et al.

(10) Patent No.: US 6,623,453 B1
(45) Date of Patent: Sep. 23, 2003

(54) CHEMO-THERMO APPLICATOR FOR CANCER TREATMENT

(75) Inventors: Raul Guibert, Falls Church, VA (US); Bettina Guibert, Falls Church, VA (US)

(73) Assignee: Vanny Corporation, Falls Church, VA (US)

(*) Notice: Subject to any disclaimer, the term of this patent is extended or adjusted under 35 U.S.C. 154(b) by 0 days.

(21) Appl. No.: 10/016,251

(22) Filed: Dec. 12, 2001

Related U.S. Application Data

(63) Continuation-in-part of application No. 09/487,434, filed on Jan. 19, 2000, now Pat. No. 6,328,711.

(51) Int. Cl.$^7$ .............................................. A61M 29/00
(52) U.S. Cl. ........................ 604/103.01; 604/101.02; 604/103.06; 607/105; 607/107
(58) Field of Search .................... 604/96.01, 103.01, 604/103.02, 103.08, 507, 514; 606/27, 190, 108, 194; 607/96, 104, 105, 107, 113, 101

(56) References Cited

U.S. PATENT DOCUMENTS

| | | | | |
|---|---|---|---|---|
| 2,734,508 A | * | 2/1956 | Kozinski | 607/105 |
| 4,398,535 A | * | 8/1983 | Guibert | 128/399 |
| 4,595,008 A | * | 6/1986 | Guibert | 128/399 |
| 4,708,718 A | * | 11/1987 | Daniels | 604/53 |
| 4,754,752 A | * | 7/1988 | Ginsburg et al. | 128/303.12 |
| 5,443,487 A | | 8/1995 | Guibert et al. | 607/101 |
| 5,624,392 A | * | 4/1997 | Saab | 604/43 |
| 5,876,743 A | | 3/1999 | Ibsen et al. | 424/426 |
| 6,149,574 A | * | 11/2000 | Trauthen et al. | 600/3 |
| 6,328,711 B1 | * | 12/2001 | Guibert et al. | 604/103.01 |

* cited by examiner

*Primary Examiner*—Brian L. Casler
*Assistant Examiner*—Jennifer Maynard
(74) *Attorney, Agent, or Firm*—Morgan, Lewis & Bockius LLP

(57) ABSTRACT

A chemo-thermo applicator insertable into a tubular membrane in the body of an individual to occupy a site therein in which the surface of the membrane is disrupted by cancerous lesions. The applicator includes concentric inner and outer tubular balloons in which the annular space therebetween is filled with a chemotherapy supply the outer balloon being perforated. In operation, a stream of heated air is fed into the inner balloon which acts to inflate this balloon and to heat the supply to cause it to melt and form a cream. Inflation of the inner balloon acts to expand the outer balloon causing it to conform to the surface of the membrane. The pressure imposed on the supply as the inner balloon expands, forces the heated cream to extrude through the outer balloon perforations to coat the surface of the membrane with the heated cream which then functions as a chemo-thermo agent to destroy the cancerous lesions.

6 Claims, 4 Drawing Sheets

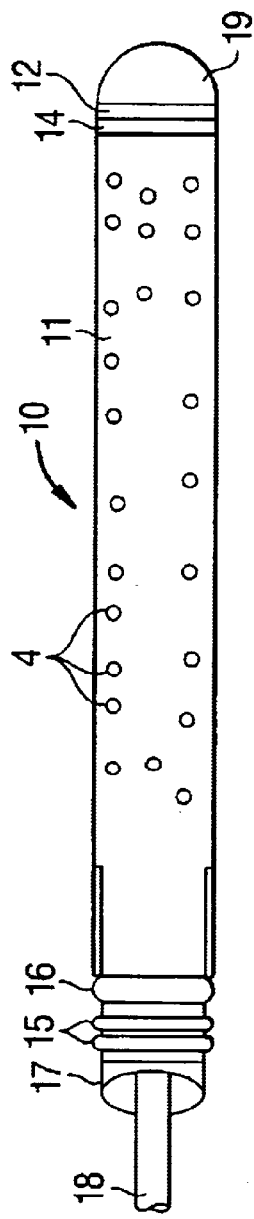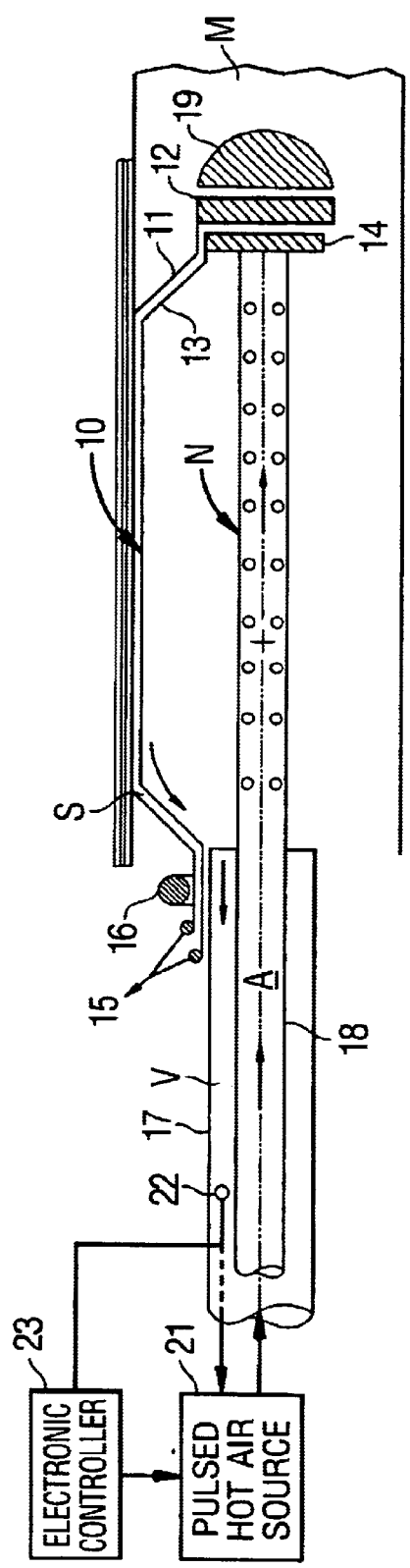

CHEMO-THERMO APPLICATOR FOR CANCER TREATMENT

This application is a Continuation-In-Part of U.S. application Ser. No. 09/487,434, filed Jan. 19, 2000, now U.S. Pat. No. 6,328,711.

BACKGROUND OF INVENTION

1. Field of Invention

This invention relates generally to devices for treating cancer, and more particularly to an applicator for this purpose which synergistically combines the positive effects of hyperthermia and chemotherapy to destroy cancerous lesions.

2. Status of Prior Art

It has long been recognized that by heating a malignant tumor to a higher temperature than that of tissues surrounding the tumor whose temperature is at normal body temperature, this action destroys the tumor. The effectiveness of such hyperthermia depends on the fact that cancers have poor circulation and a reduced ability to dissipate heat. Thus a temperature of no more than 115 degrees Fahrenheit is capable of destroying cancer cells while sparing healthy tissues.

The 1983 U.S. Pat. No. 4,398,535 to Guibert discloses a hyperthermia technique for destroying a malignant tumor whose site in the body of an individual is within an internal region underlying the surface of the skin. Applied to the surface of the skin is a stream of air which is heated to produce an air wave having periodic pulses whose peak temperature is well-above body temperature, the intervals between these pulses being at an air temperature just above body temperature.

As a consequence, heat from the high temperature pulse in the stream of air flowing over the surface of the skin is conductively transferred from the skin during the lower-temperature intervals to the tumor in the internal region below the skin, thereby raising the temperature of the tumor to a level which destroys it. But because the skin surface is subjeced to relatively long low-temperature intervals between the high-temperature pulses, the cooling which takes place during these intervals results in a skin temperature which is never raised to an unsafe degree.

Also of prior art interest is the 1995 Guibert et al. Pat. No. 5.443,487. This patent discloses a combined chemo-thermo therapy technique in which a pharmaceutical agent, such as a lipolysis cream, is topically applied to a localized skin surface overlying a problem region to be treated. This surface is then subjected to an air stream whose temperature alternates periodically from a high peak level to a lower base level in a pulsatory heat energy wave pattern. Because heat transfer takes place under the skin in the intervals between successive peaks, the temperature of the problem region containing the tumor is significantly raised, but that on the skin surface remains at a tolerable level. As a consequence, the absorption of the agent and its diffusion throughout the tissue of the heated problem region is accelerated and its interaction therewith is promoted to enhance the effectiveness of the treatment.

The concern of the present invention is with the treatment of cancerous lesions disposed in an internal region of the body that is not accessible to hyperthermic apparatus of the type disclosed in the above-identified Guibert patents in which a stream of heated air is applied to a skin area overlying an internal region having a malignant tumor therein.

Typical of a region which is not accessible to the prior Guibert apparatus is the colon, for should there be malignant tumors on the mucosa of the colon, one could not then destroy these tumors by applying pulsed heat to a skin area of the body. The site of the colon in the body is so distant from the skin surface, that if a stream of heated air were applied to this skin surface, the heat in the course of its transfer from the skin surface to the colon would be dissipated in the intervening tissues of the body, and would never reach the colon.

The colon is a large intestine extending from the cecum to the rectum. Although the colon is a continuous hollow muscular tube, it is divided into several sections, namely the ascending colon, the transverse colon and the descending colon. As it enter the pelvis, the colon makes a double curve similar to the letter S, this being known as the sigmoid colon. The end of the sigmoid colon terminates at the rectum. The rectum and the colon constitute a meandering passage having a tubular membrane. In order therefore for an applicator or other device to reach a remote site in the tubular membrane of the colon, the applicator must snake its way through the passage. Thus a flexible fiberoptic sigmoidoscope can make its way well into the colon to detect cancerous tissues.

In the United States, the colon and rectum account for more cancer cases each year than any other anatomic site, other than the lungs. The primary treatment for colon cancer consists of a surgical resection of the lesions. But surgical treatment for colon cancer is not a permanent cure and often does not prevent a recurrence of the cancer.

According to the Merck Manual (15$^{th}$ Edition, page 819), chemotherapy has not proven to be effective as a surgical adjuvant in clinical trials of colon and rectal cancers. And studies of adjuvant radiation therapy, after curative cancer surgery, indicate that such radiation only delays the recurrence of the cancer.

SUMMARY OF INVENTION

In view of the foregoing, the main object of this invention is to provide a chemo-thermo applicator insertable in a tubular membrane within an individual to a site therein at which the surface of the membrane is disrupted by cancerous lesions, the applicator serving to destroy these lesions.

Among the significant advantages of an applicator in accordance with the invention are the following:

A. The applicator is capable of snaking its way into a meandering tubular membrane so that it can be placed at the site of the cancerous lesions to be destroyed.

B. In operation, the applicator synergistically combines the positive therapeutic effects of hyperthermia and chemotherapy to destroy there cancerous lesions.

C. The thermal energy applied by the applicator to the cancerous lesions is adjustable to attain optimal conditions of treatment without damaging healthy tissues.

Also an object of this invention is to provide an applicator of the above type which includes a tubular balloon whose diameter is such as to permit the applicator to easily pass through a meandering tubular membrane, which balloon when the applicator is at a desired site can then be expanded to engage the surface of the membrane.

Briefly stated, these objects are attained by an insertable into a tubular membrane in the body of an individual to occupy a site therein in which the surface of the membrane is disrupted by cancerous lesions. The applicator includes concentric inner and outer tubular balloons in which the annular space therebetween is filled with a chemotherapy supply, the outer balloon being perforated.

In operation, a stream of heated air is fed into the inner balloon which acts to inflate this balloon and to heat the supply to cause it to melt to form a cream. Inflation of the inner balloon acts to expand the outer balloon causing it to conform to the surface of the membrane. The pressure imposed on the supply as the inner balloon expands, forces the cream heated to extrude through the outer balloon perforations to coat the surface of the membrane with the heated cream which then functions as a chemo-thermo agent to destroy the cancerous lesions.

BRIEF DESCRIPTION OF DRAWINGS

For a better understanding of the invention as well as other objects and further features thereof, reference is made to the following detailed description to be read in conjunction with the accompanying drawings, wherein:

FIG. 1 illustrates a preferred embodiment of a chemo-thermo applicator in accordance with the invention in its uninflated state;

FIG. 2 is a section taken through the applicator in its inflated state within a tubular membrane in the body of an individual being treated;

DESCRIPTION OF SPECIFIC EMBODIMENTS

Figure 3:
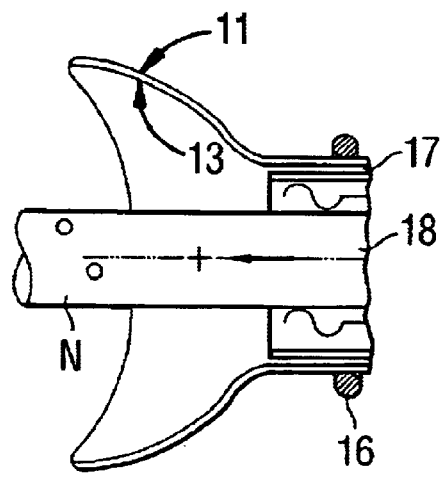
FIG. 3 is a partial view of the inner and outer balloons of the applicator in its inflated state.
Figure 4:
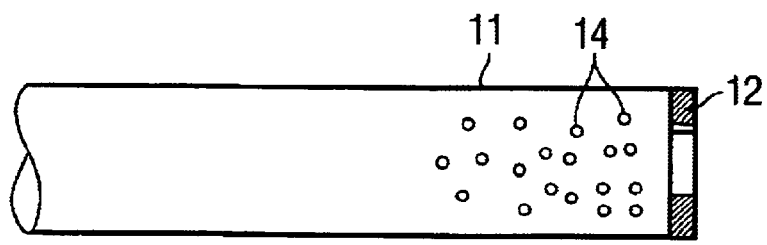
FIG. 4 illustrates the assembly of the inner and outer balloons.
Figure 5:
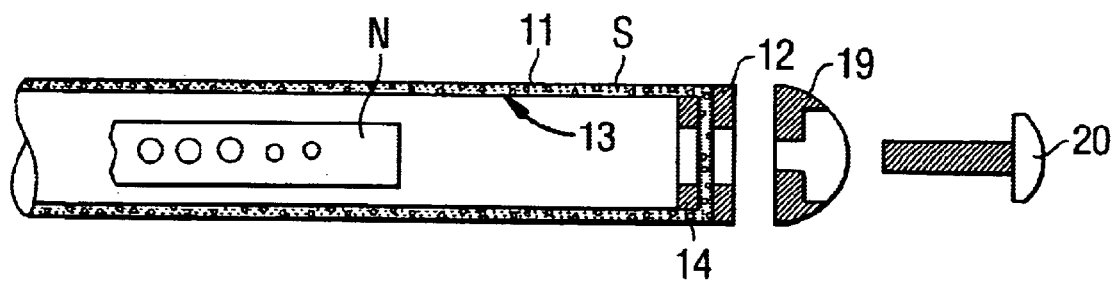
FIG. 5 illustrates how to assemble one embodiment of the device.

Referring now to FIGS. 1 and 2, shown therein is a preferred embodiment of an applicator 10 in accordance with the invention. It includes an outer tubular balloon 11 that is condom-like, balloon 11 normally having a cylindrical shape of uniform diameter. Balloon 11 is circumferentially perforated to create small holes H that are uniformly distributed throughout the balloon.

Outer balloon 11 which is fabricated of stretchable latex or similar elastic material of good strength is bonded at its front end to an annular mounting disc 12 of the same diameter. Concentric with outer balloon 11 and formed of the same material is an inner balloon 13 is impervious to air, hence it is inflatable. Inner balloon is which of somewhat smaller diameter then outer balloon 11 is bonded to an annular mounting disc 14 of the same diameter.

The narrow annular space S between concentric balloons 11 and 13 has deposited therein a supply of an anti-cancer thermotherapy agent that is appropriate to the cancer that is to be treated by the applicator; such as an antitumor antibiotic, a plant alkaloid or an antimetabolite agent.

At body temperature, the chemotherapy agent in supply S is in a semi-solid state. But when heated to a temperature level that is effective in destroying cancerous lesions (say 120 degrees F.) it then softens and melts to form a cream that can be extruded through holes H in the outer balloon.

To assemble the applicator, a plastic nose piece 19 is joined to the annular mounting discs 12 and 14 of the outer and inner balloons 11 and 13 by a plug 20.

Telescoped into the rear ends of the concentric inner and outer balloons 11 and 13 is the leading end of a coaxial hose 17 formed of flexible synthetic plastic material, the rear ends of the balloons being clamped to the hose by O rings 15 and 16. Coaxially supported within hoses 17 is an inner pipe 18 of flexible plastic material which projects beyond the leading end of hose 17 into the tubular inner balloon 13. The projecting portion of pipe 18 is perforated to create a nozzle N from which a heated air stream is discharged into inner balloon 13.

Coaxial hose 17 which has a relatively long length couples applicator 10 to an external heated air source 21 which functions to pump a stream of heated air A into inner pipe 18, the stream being disclosed by nozzle N into inner balloon 13. The heated air stream which acts to inflate the inner balloon, as shown in FIGS. 2 and 3, is returned to source 21 through the annular flow passage V between outer hose 17 and its coaxial inner pipe 17. Thus the flow of heated air through the inner balloon is in a continuous circulating loop in which air temperature air is determined and controlled by source 21.

Heated air source 21 is preferably of the pulsatory wave type disclosed in the above identified Guibert patents. This air heat-energy wave is in a pulsatory heat pattern created by air pulses having high-temperature peaks and intervals between the pulses having a lower temperature. The temperature pattern of the stream inflating the inner balloon is such as to effect the transfer of heat to the surface of the tubular membrane being heated by the applicator to elevate the temperature of the cancerous lesions disrupting the surface to a level that is destructive of the lesions without raising the temperature of the surface which is free of lesions to a destructive level.

The diameter of applicator 10 in its uninflated state, as shown in FIG. 1, and of hose 17 extending extending therefrom is smaller than the internal diameter of the tubular membrane M into which applicator 10 is inserted. Hence even when, as in a colon, the tubular membrane therein has aa meandering path, it is not difficult to snake the applicator through the membrane to reach a site therein, as shown in FIG. 2, in which the surface of the membrane is disrupted by cancerous lesions.

When applicator 10 is at the desired site in membrane M, it is then put into operation by feeding a stream of heated air from source 21 into the inner balloon 13 which acts to inflate this balloon, as shown in FIGS. 2 and 3. The inflated inner balloon expands the perforated outer balloon 11 to cause it to conform to the surface of the membrane to be treated. Supply S of the chemotherapy agent surrounding the inner balloon is heated by the heated air flowing through the inner balloon.

This heated air preferably has a high relative humidity in order to increase the heat capacity of the atmosphere within the inner balloon. And in practice, the thermal conductivity of the inner balloon may be enhanced by dispersing in the latex of the inner balloon fine graphite or other thermally conductive particles.

Heat transferred from inner balloon 13 to the chemotherapy agent in supply S acts to heat and melt this anti-cancer agent to form a cream. And the pressure applied by the inner balloon to this cream acts to extrude it through holes H in outer balloon 11 which is expanded to conform to the surface of the membrane M. This extrusion causes the heated cream to coat the lesions on the surface of the membrane.

The heated chemotherapy coating on the lesion serves two functions. The first is hyperthermic which elevates the temperature of the cancerous lesions to a level which is destructive thereof. These chemo and thermo actions are synergistic in nature, for the hyperthermia acts to elevate the temperature of the cream and enhance its effectiveness as a chemotherapy agent to destroy the lesions.

To maintain the heated circulating air stream at a desired temperature level, a thermister 22 or other heat sensor is disposed in the return passage V in the coaxial hose 17, sensor 22 yielding a signal that depends on the temperature of the air stream passing through this passage. This signal is applied to an electronic controller 23 having an adjustable set point. Controller 23 compares the signal with the set point to determine the extent to which the temperature of the stream deviates from the set point and acts to yield a control signal which is applied to the heated air source to adjust the temperature of the air stream so that it is at the desired set point temperature level.

The embodiment of the applicator illustrated in the drawing is a chemo-thermo applicator, for it synergistically combines a hyperthermia anti-cancer action with a chemotherapy anti-cancer action.

In practice, the applicator can be simplified to provide only a hyperthermia action. In that event, the applicator only includes a single tubular balloon which is insertable into a tubular membrane in the body of an individual to a site at which the surface of the membrane is disrupted by cancerous lesions. The single balloon is then inflated by heated air to conform to this surface and to transfer heat to the surface to destroy the lesions.

Figure 6:
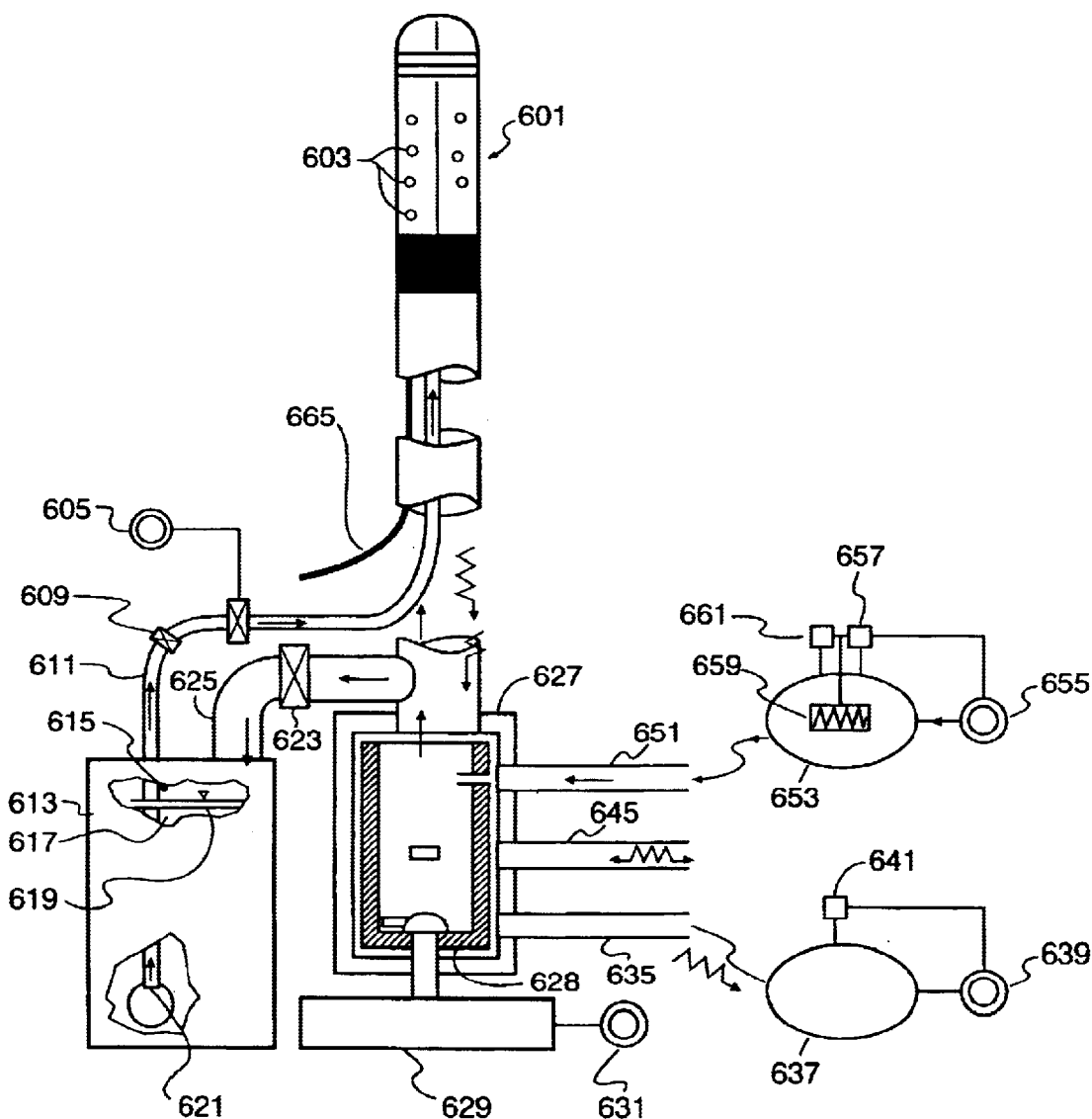
FIG. 6 illustrates an embodiment with automatic, cyclical administration of the medication.

FIG. 6 depicts an embodiment wherein the applicator 601 has holes 603 of a diameter, and in a number, dependent on the viscosity of the cream medication at the application temperature (e.g., 70° F. requires larger and/or more holes, whereas 135° F. requires smaller and/or fewer holes). The flow of heated air (or steam) to the applicator can be controlled by a timer 605 activating a switch or solenoid 607; a check valve 609 is shown and preferred.

The tube 611 supplying the medication to be administered is preferably provided as a separate container 613, which can be manufactured by a third party company, supplied to the treatment center specifically for a given patient or condition to be treated, and hooked up between the applicator and the pneumatic source by standard couplings (not shown). The container has an air chamber 615 and a medicament chamber 617 separated by a plenum or membrane 619, such that air force in the air chamber forces the medicament through the opening 621 into and through tube 611.

Air is supplied to the container through a check valve 623 in a conduit 625 via plenum 627 housing rotor valve 628 powered by electric motor 629; the motor is controlled by a control device 631. The rotor valve is preferrably controlled to provide a desired air throughput and rate, and cycling of the can be provided by an associated conventional timing circuit in or associated with the control device to provide pulses of air. Low pressure air evacuated from the applicator conduit and pump exits through conduit 635 into reservoir 637, which has its pressure maintained by a vacuum pump 639 controlled by a pressure sensor and control device 641. Reference or room pressure air is provided to the pump via conduit 645. High pressure air is provided to the pump via conduit 651 from reservoir 653, the pressure being maintained by pump 655 and controlled by pressure sensing and control device 657. Where the high pressure air is heated, a heater 659 is provided in the reservoir and controlled by temperature sensor and controller 661. One or more of the sensing and control devices, if not all, include an associated display so that the temperature and/or pressure is displayed to the physician.

Figure 7:
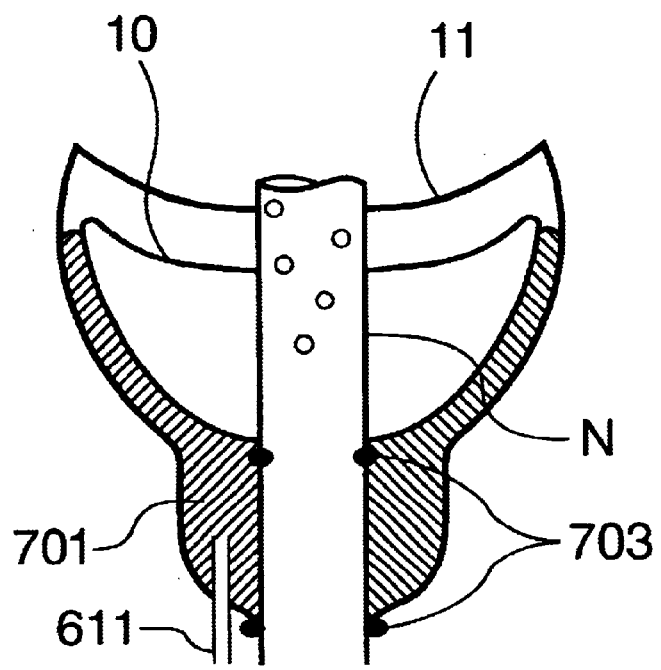
FIG. 7 illustrates a partial view of the inner and outer ballons of the applicator shown in FIG. 6.

FIG. 7, viewed in conjunction with FIGS. 1 and 2, provides a cutaway view similar to FIG. 3. In the embodiment in FIG. 7, there is no recirculation of the air; rather, the air exits though conduit 645 to the surroundings, or prior to release into the room is filtered and/or sterilized to maintain the cleanliness of the surroundings. The medicament cream 701 is shown between the inner 10 and outer 11 baloons. O-rings 703 secure each of the openings of the balloons. The medicament tube 611 preferably ends in the space between the two balloons, and can pass through the outer balloon by virtue of a nipple or similar close-fitting conduit in (passing through) the outer balloon.

Figure 8:
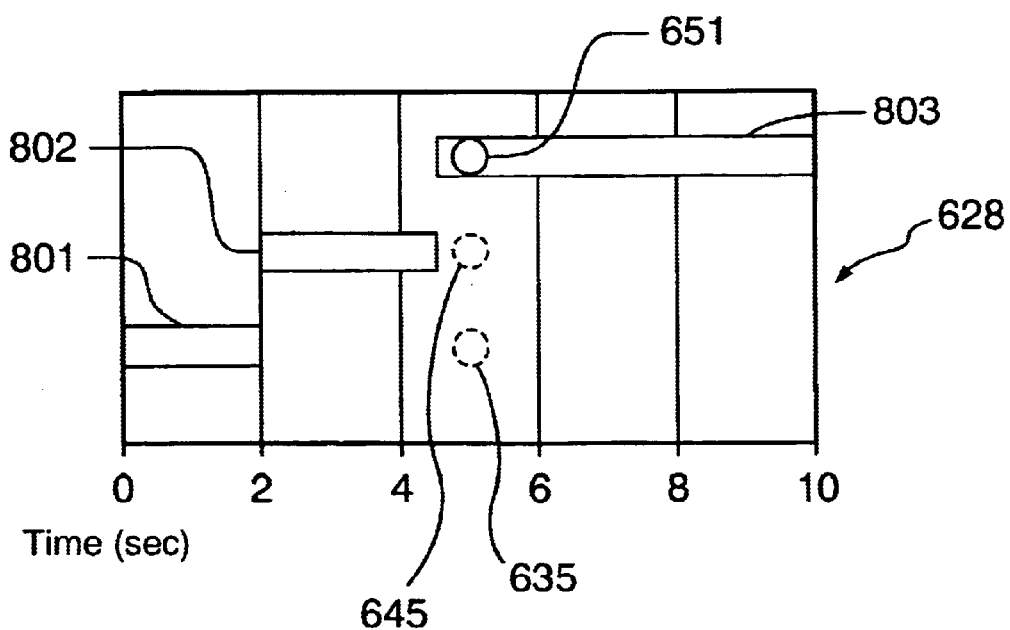
FIG. 8 is an idealized view of the rotor valve and the ports in the air supply plenum showing their respective timings.

FIG. 8 depicts the cylindrical rotor 628 in the cylindrical housing or plenum 627 and the associated air passages 635, 645, and 651, as if the rotor (and housing) had been opened and flattened. FIG. 8 divides the circumference (or ordinate in the figure) into time intervals; in practical terms, such can be accomplished with the control device 631. As the rotor starts to turn, for the first 2 seconds, the low pressure reservoir connects to the plenum via opening 801 (the sealing means between the rotor and the housing, and between the air passages and the rotor, are not shown) for about two seconds. Thereafter, for about three seconds, the plenum is vented to atmosphere as opening 802 uncovers passage 645. Finally, opening 803 uncovers passage 651 connecting the balloon through the plenum with the heated, pressurized air. Of course, it should be understood that steam or an atomized medicament can also be provided to the applicator via the plenum. Thus, the check valves 607 and 623 are required to prevent backflow when the plenum has a lower relative pressure. Of course, beside the rotor, a electronic timing device can be used to separately open and close valves for each of the passages, optionally one that is microprocessor controlled, and any of the valve actuators can be electronic or pneumatic. However, a mechanically operated valving system is preferred for its simplicity and fault-tolerance.

Optionally, as shown in FIG. 6, a fiber optic cable 665 can be used to visualize the conditions at the applicator. Additionally, the applicator can be provided with a channel extending through the ballon area and out through the top/front of the applicator, whereby the physician can visualize the field within the body membrane beyond the applicator.

The present invention can be used alone to treat a condition such as cancer, or depending on the particular patient, can be used in combination with radiation therapy, or chemotherapy, or all three can be used, either sequentially, alternating, or simultaneously.

While there has been disclosed preferred embodiments of a chemo-thermo applicator in accordance with the invention, it will be appreciated that many changes may be made therein without departing from the spirit of the invention.

We claim:

1. An applicator insertable into a cavity in the body of an individual to occupy a site therein at which the surface of the cavity is disrupted by lesions, the applicator comprising:
   A. an inner tubular balloon which normally has a diameter smaller than that of the cavity whereby the applicator can travel through the cavity to said site and an outer, porous, tubular balloon disposed over the inner balloon and having a diameter smaller than that of the cavity;
   B. means to feed a pressurized and optionally heated air stream into the balloon to inflate the inner balloon and cause it to expand, and the expansion of the inner balloon effective to dispense a flowable composition through the openings in the outer balloon, said expansion also causing the balloons to conform to a surface of the cavity, optionally applying heat thereto and transfering heat from said heated air stream to said lesions acting to raise the temperature of the lesions to a level destructive of the lesions;

and at least one of

C.1. a container having separate connections to (a) said means for feeding a heated air stream and (b) a space between said inner and outer balloons, said container including a plenum separating a section of the container housing said composition and said means, whereby said means forces the composition, via the plenum, into said space between the inner and outer balloons; and C.2. said means comprising a plenum having separate connections to (a) a high pressure air source, (b) a low pressure air source, and (c) a vent, and means for providing and controlling fluid communication between said plenum and each of (a), (b), and (c).

2. The applicator of claim 1, comprising both C.1. and C.2.

3. The applicator as set forth in claim 1, further comprising means for providing in the air stream a pulsatory pattern formed by periodic pulses having a relatively high peak temperature and intervals therebetween having a lower temperature.

4. The applicator of claim 1, wherein C.2. comprises a cylindrical housing having three inlets, said housing having an inner wall defining an interior space with which the inlets communicate, and a rotatable cylindrical valve disposed within the housing and co-axial with the axis of the housing, the valve providing a seal between the interior space and each of the three inlets, and openings in the valve corresponding with each of the inlets, whereby rotation of the valve alternatively seals the inlets or positions an opening over a corresponding inlet.

5. A method for treating a lesion in a body cavity, comprising:

A. providing an inner tubular balloon which normally has a diameter smaller than that of the cavity whereby an applicator comprising said inner balloon is inserted through the cavity to said site and said applicator further comprising an outer, porous, tubular balloon disposed over the inner balloon and having a diameter smaller than that of the cavity;

B. providing a means to feed a pressurized and optionally heated air stream into the balloon to inflate the inner balloon and cause it to expand, the expansion of the inner balloon effective to dispense a flowable composition through the openings in the outer balloon, said expansion also causing the balloons to conform to a surface of the cavity, optionally applying heat to the cavity wall and transferring heat from the heated air stream to the lesions at a temperature destructive to the lesions; and at least one of C.1. providing a container in fluid connection between the pressurized and optionally heated air stream and the applicator via separate connections to each, said container including a plenum separating a section of the container housing said composition and said means, whereby said pressurized air forces the composition, via the plenum, into said space between the inner and outer balloons; and C.2. valving the pressurized and optionally heated air stream by means of a cylindrical housing having three inlets, said housing having an inner wall defining an interior space with which the inlets communicate, and a rotatable cylindrical valve disposed within the housing and co-axial with the axis of the housing, the valve providing a seal between the interior space and each of the three inlets, and openings in the valve corresponding with each of the inlets, whereby rotation of the valve alternatively seals the inlets or positions an opening over a corresponding inlet.

6. The method of claim 5, wherein said container is replaceable.

* * * * *